United States Patent
Datta et al.

(10) Patent No.: US 12,213,728 B2
(45) Date of Patent: Feb. 4, 2025

(54) TEMPERATURE CONTROLLED SHORT DURATION ABLATION WITH RESISTIVE HEATING

(71) Applicant: BIOSENSE WEBSTER (ISRAEL) LTD., Yokneam (IL)

(72) Inventors: Keshava Datta, Chino Hills, CA (US); Kristine Fuimaono, Costa Mesa, CA (US); Assaf Govari, Haifa (IL); Andres Claudio Altmann, Haifa (IL); Tushar Sharma, Arcadia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 957 days.

(21) Appl. No.: 16/856,458

(22) Filed: Apr. 23, 2020

(65) Prior Publication Data

US 2020/0345414 A1 Nov. 5, 2020

Related U.S. Application Data

(60) Provisional application No. 62/841,754, filed on May 1, 2019.

(51) Int. Cl.
*A61B 18/00* (2006.01)
*A61B 18/14* (2006.01)

(52) U.S. Cl.
CPC ............... *A61B 18/1492* (2013.01); *A61B 2018/00577* (2013.01); *A61B 2018/00738* (2013.01); *A61B 2018/00761* (2013.01); *A61B 2018/00791* (2013.01)

(58) Field of Classification Search
None
See application file for complete search history.

(56) References Cited

U.S. PATENT DOCUMENTS

| 5,788,636 | A | * | 8/1998 | Curley | A61B 18/1206 606/31 |
| 5,833,688 | A | * | 11/1998 | Sieben | A61B 18/1492 606/41 |
| 7,207,989 | B2 | | 4/2007 | Pike, Jr. et al. | |
| 8,641,705 | B2 | | 2/2014 | Leo et al. | |
| 8,882,761 | B2 | | 11/2014 | Desai | |
| 10,292,763 | B2 | | 5/2019 | Govari et al. | |

(Continued)

FOREIGN PATENT DOCUMENTS

JP 2002-065690 A 3/2002
WO WO2014197625 A1 12/2014

OTHER PUBLICATIONS

European Search Report for corresponding EPA No. 20172274.1 dated Sep. 29, 2020.

(Continued)

*Primary Examiner* — Thomas A Giuliani
*Assistant Examiner* — Nicholas S Borsch
(74) *Attorney, Agent, or Firm* — Frost Brown Todd LLP (57) ABSTRACT

A method, including performing an ablation of tissue using a first high RF power for a short duration, suspending RF power for a predetermined period, and using a second high RF power for a short duration forming lesions with greater surface area and greater depth through resistive heating and thermal latency. High RF power may range between 75-95 W and short duration may range between 4-5 seconds.

6 Claims, 6 Drawing Sheets

(56) References Cited

U.S. PATENT DOCUMENTS

| | | | |
|---|---|---|---|
| 10,307,206 B2 | 6/2019 | Govari et al. | |
| 10,405,920 B2 | 9/2019 | Govari et al. | |
| 10,441,354 B2 | 10/2019 | Govari et al. | |
| 11,172,984 B2* | 11/2021 | Sharma | A61B 18/1492 |
| 2010/0057072 A1 | 3/2010 | Roman et al. | |
| 2011/0009857 A1 | 1/2011 | Subramaniam et al. | |
| 2011/0130648 A1 | 6/2011 | Beeckler et al. | |
| 2012/0136354 A1* | 5/2012 | Rupp | A61B 18/1206 606/51 |
| 2014/0171821 A1 | 6/2014 | Govari et al. | |
| 2015/0272655 A1 | 10/2015 | Condie et al. | |
| 2017/0143401 A1* | 5/2017 | Woloszko | A61B 18/1206 |
| 2017/0209208 A1* | 7/2017 | Govari | A61B 18/1206 |
| 2017/0209209 A1* | 7/2017 | Govari | A61B 18/1492 |
| 2017/0312025 A1* | 11/2017 | Harlev | A61M 3/0295 |
| 2019/0008588 A1 | 1/2019 | Davies | |

OTHER PUBLICATIONS

Topp, MD, Stefan A., et al., "Saline-Linked Surface Radiofrequency Ablation Factors Affecting Steam Popping and Depth of Injury in the Pig Liver," Ann.Surg., vol. 239, No. 4, pp. 518-527, Apr. 2004.
Japanese First Office Action dated Nov. 21, 2023, for Application No. 2020-080060, 3 pages.
Japanese Final Office Action dated May 14, 2024, for Application No. 2020-080060, 2 pages.

* cited by examiner

TEMPERATURE CONTROLLED SHORT DURATION ABLATION WITH RESISTIVE HEATING

CROSS-REFERENCE TO RELATED APPLICATION(S)

This application claims priority to and the benefit of U.S. Provisional Patent Application No. 62/841,754, filed May 1, 2019, the entire content of which is incorporated herein by reference.

FIELD OF THE INVENTION

The present invention relates generally to surgery, and specifically to surgery using radiofrequency ablation.

BACKGROUND OF THE INVENTION

Radiofrequency (RF) ablation is a treatment modality that kills unwanted tissue by heat. Starting with cardiac arrhythmia treatment in the 1980s, RF ablation has found clinical application in a number of diseases, and is now the treatment of choice for certain types of cardiac arrhythmia, and certain cancers. During RF ablation, an electrode is inserted into proximity with the target region under medical imaging guidance. Tissue surrounding the electrode in the target region is destroyed by heating via RF electric current.

RF ablation is typically performed at continuous power levels of the order of 20-50 watts, with a contact force of approximately 10 g, and under irrigation. The time of ablation, depending on the size of the lesion to be achieved, is typically approximately 1 minute. In general, higher power levels reduce the time needed for forming a specific lesion. However, in prior art systems large values of continuous power cannot be used because of the danger of steam pops being formed.

US Patent Application 2010/0057072, to Roman et al., whose disclosure is incorporated herein by reference, describes an ablation catheter for performing tissue ablation. The disclosure states that RF energy may be safely delivered potentially at wattages up to 100 W.

U.S. Pat. No. 7,207,989, to Pike Jr. et al., whose disclosure is incorporated herein by reference, describes a method for ablating tissue in or around the heart to create an enhanced lesion. The distal end of a needle electrode is introduced into the tissue. An electrically-conductive fluid is infused through the needle electrode and into the tissue. The tissue is ablated after and/or during introduction of the fluid into the tissue.

US Patent Application 2015/0272655, to Condie et al., whose disclosure is incorporated herein by reference, describes a system for preventing unintended tissue damage from the delivery of unintended bipolar radiofrequency energy. The disclosure states that if 100 watts of RF energy is being delivered but only 10 watts is required to produce a desired electrode temperature, an electrode may be activated for 10% of a given period of time and deactivated for 90% of that duration of time.

U.S. Pat. No. 8,641,705, to Leo et al., whose disclosure is incorporated herein by reference, describes an apparatus for controlling lesion size in catheter-based ablation treatment. The apparatus measures the force exerted by a contact ablation probe on a target tissue and integrates the force over an energization time of the ablation probe. The force-time integral can be calculated and utilized to provide an estimated lesion size (depth, volume and/or area) in real time.

U.S. Pat. No. 8,882,761, to Desai, whose disclosure is incorporated herein by reference, describes a catheter for ablation. The disclosure refers to commonly practiced ablation procedure, and states that in such a procedure 35 to 50 watts of power is delivered at 40 to 50 degree Celsius through a temperature controlled Radiofrequency Generator, and that the saline irrigation fluid rate during the ablation is 30 ml/min.

US Patent Application 2011/0009857, to Subramaniam et al., whose disclosure is incorporated herein by reference, describes an open-irrigated catheter with turbulent flow. Pressurized fluid is delivered from a fluid lumen of a catheter body into an ablation electrode. Fluid flow in the fluid lumen is generally laminar. The generally laminar fluid flow is transformed from the fluid lumen into a turbulent fluid flow within the ablation electrode.

In an article by Topp et al., entitled "Saline-linked surface radiofrequency ablation: Factors affecting steam popping and depth of injury in the pig liver," Ann. Surg., vol. 239, no. 4, pp. 518-27 (2004), the authors claim to have determined parameters that predict steam popping, and depth of tissue destruction under nonpopping conditions. The article is incorporated herein by reference.

U.S. patent application Ser. Nos. 15/179,090, 15/179,129, 15/179,167 and 15/179,196, each with the title TEMPERATURE CONTROLLED SHORT DURATION ABLATION and filed Jun. 10, 2016, whose disclosures are incorporated herein by reference, describe methods for ablation, including a method comprising selecting a first maximum radiofrequency (RF) power to be delivered by an electrode within a range of 70 W-100 W, and selecting a second maximum RF power to be delivered by the electrode within a range of 20 W-60 W. The method also includes selecting an allowable force on the electrode within a range of 5 g-50 g, selecting a maximum allowable temperature, of tissue to be ablated, within a range of 55° C.-65° C., and selecting an irrigation rate for providing irrigation fluid to the electrode within a range of 8-45 ml/min. The method further includes performing an ablation of tissue using the selected values by initially using the first power, switching to the second power after a predefined time between 3 s and 6 s, and terminating the ablation after a total time for the ablation between 10 s and 20 s.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

In some embodiments, a method of ablation includes:
inserting a catheter into a subject, the catheter having an ablation electrode configured for tissue contact;
performing an ablation session on the tissue for a predetermined total duration of time, including:
applying radiofrequency (RF) power via the electrode within a range of about 75 W-95 W that induces resistive heating for a first duration to form a lesion having a first depth;
suspending application of RF power to the electrode for a second duration; and reapplying RF power via the electrode to the lesion within a range of about 75 W-95 W for a third duration to increase lesion to a second depth.

In some embodiments, the first duration is about 4 seconds.

In some embodiments, the second duration no greater than about 10 seconds.

In some embodiments, the second duration is about 4 seconds.

In some embodiments, the second duration is about 5 seconds.

In some embodiments, the third duration is about 4 seconds.

In some embodiments, the total duration is less than about 18 seconds.

In some embodiments, the total duration is less than about 13 seconds.

In some embodiments, the first depth is about 3.5 mm.

In some embodiments, the second depth is about 4.5 mm.

In further embodiments, a method of ablation includes:
  inserting a catheter into a subject, the catheter having an ablation electrode configured for tissue contact;
  performing an ablation session on the tissue for a predetermined total duration of time, including:
    applying resistive heating by radiofrequency (RF) power via the electrode within a range of about 75 W-95 W for a first duration to form a lesion with a depth of about 3.5 mm;
    suspending application of RF power to the electrode for a second duration to allow tissue surrounding the lesion to heat by conduction from the lesion; and
    while the tissue surrounding the lesion remains heated by conduction from the lesion, reapplying resistive heating by RF power via the electrode within the range of about 75 W-95 W for a third duration to the lesion to increase depth of the lesion to about 4.5 mm.

In other embodiments, a method of ablation includes:
  inserting a catheter into a subject, the catheter having an ablation electrode configured for tissue contact;
  performing an ablation session on the tissue for a predetermined total duration of time of less than about 13 seconds, including:
    applying radiofrequency (RF) power to induce resistive heating via the electrode within a range of about 75 W-95 W for about 4 seconds to form a lesion;
    suspending application of RF power to the electrode for no greater than about 5 seconds to allow tissue surrounding the lesion to heat by conduction from the lesion; and
    while the tissue surrounding the lesion remains heated by conduction from the lesion, reapplying RF power to induce resistive heating via the electrode to the lesion within a range of about 75 W-95 W for about 4 seconds to increase depth of the lesion.

In alternate embodiments, a method of ablation includes:
  inserting a catheter into a subject, the catheter having an ablation electrode configured for tissue contact;
  performing an ablation session on the tissue for a predetermined total duration of time of less than about 13 seconds, including:
    applying radiofrequency (RF) power by resistive heating via the electrode to form a lesion having a depth of about 3.5 mm;
    suspending application of RF power to the electrode to allow tissue surrounding the lesion to heat by conduction from the lesion; and
    while the tissue surrounding the lesion remains heated by conduction from the lesion, reapplying RF power by resistive heating via the electrode to increase depth of the lesion to about 4.5 mm.

In some embodiments, the RF power is about 90 W.

In further embodiments, a method of ablation includes:
  inserting a catheter into a subject, the catheter having an ablation electrode configured for tissue contact;
  performing an ablation session on the tissue for a predetermined total duration of time, including:
    applying radiofrequency (RF) power of about 360 joules via the electrode for a first duration of about 4 seconds to form a lesion having a first depth of about 3.5 mm;
    suspending application of RF power to the electrode for a second duration no greater than about 10 seconds; and
    reapplying RF power of about 360 joules via the electrode to the lesion for a third duration of about 4 seconds to increase lesion to a second depth of about 4.5 mm.

In other embodiments, a method of ablation, including:
  inserting a catheter into a subject, the catheter having an ablation electrode configured for tissue contact;
  performing an ablation session on the tissue for a predetermined total duration of time, including:
    applying radiofrequency (RF) power of about 360 joules via the electrode to form a lesion by resistive heating having a first depth of about 3.5 mm;
    suspending application of RF power to the electrode for a second duration to allow the lesion to heat surrounding tissue by conductive heating; and
    while the surrounding tissue contains conductive heating from the lesion, reapplying RF power of about 360 joules via the electrode to the lesion by resistive heating to a second depth of about 4.5 mm.

The present disclosure will be more fully understood from the following detailed description of the embodiments thereof, taken together with the drawings, in which:

DETAILED DESCRIPTION OF EMBODIMENTS

Overview

Radiofrequency (RF) ablation in prior art systems is typically performed at continuous power levels of the order of 20-50 watts, with a contact force of approximately 10 g, and under irrigation. The time of ablation, depending on the size of the lesion to be achieved, is typically approximately 1 minute. In general, higher power levels reduce the time needed for forming a specific lesion. However, in prior art systems large values of continuous power, of approximately 100 watts, cannot be used because of the danger of steam pops being formed.

The inventors have found that by applying two "pulses" of high RF power of short duration, separated by a predetermined interval of suspension of RF power, the lesion created by the first pulse can be improved with greater surface area and greater depth by the second pulse. A "sweet spot" without steam pops is achieved with the two pulses, the first of which applies a high RF power ranging between 75 W-95 W for a short duration of 4-5 secs that results in resistive heating and thermal latency in the lesion which during the interval of suspension of RF power ranging between 4 and 10 secs conducts heat to surrounding tissue so as to prime the surrounding tissue for expansion of the lesion with greater surface area and greater depth upon the application of the second pulse also of high RF power ranging between about 75-95 W for a short duration of 4-5 seconds. An allowable contact force on the electrode is selected to be in a range of 5 g-50 g, a maximum allowable temperature of tissue to be ablated is selected to be in a range of 55° C.-65° C., and an irrigation rate for providing irrigation fluid to the electrode is selected within a range of 8-45 ml/min.

In embodiments of the present invention, during an ablation procedure the temperature of the tissue being ablated is carefully monitored and recorded at an extremely high rate. If the monitored temperature exceeds a preset maximum temperature limit, the RF power supplied to the tissue is stopped or reduced.

The impedance to the RF energy supplied to the tissue being ablated is also monitored. If the impedance increases by more than a preset value, the RF energy supply is halted.

The monitoring of the temperature and of the impedance allows embodiments of the present invention to perform tissue ablations at powers up to 100 W without adverse effects on the tissue during the ablation session. The high powers enable the ablation session to be shortened to times typically of no more than 10 s.

DETAILED DESCRIPTION

Figure 1:
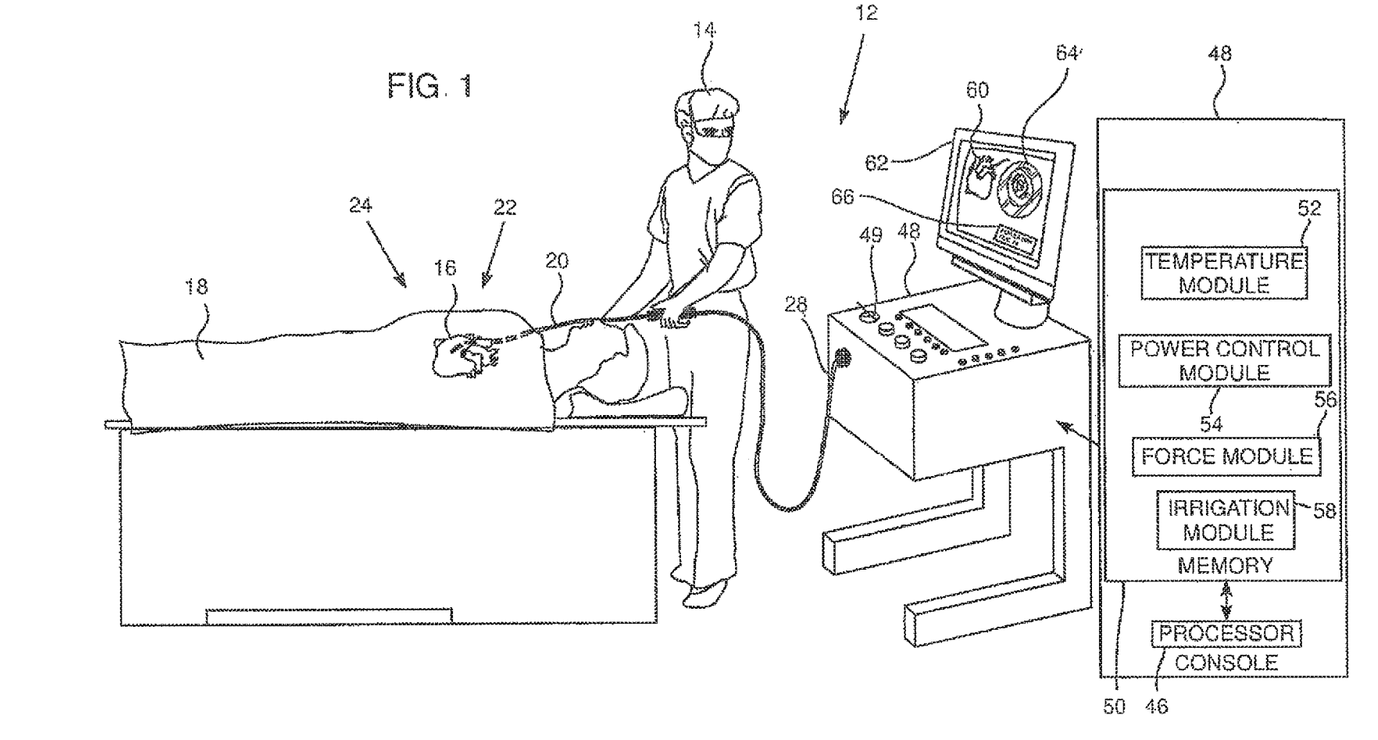
FIG. 1 is a schematic illustration of an ablation system, according to an embodiment of the present invention.

Reference is now made to FIG. 1, which is a schematic illustration of an invasive medical procedure using an ablation apparatus 12, according to an embodiment of the present invention. The procedure is performed by a physician 14, and, by way of example, the procedure in the description herein below is assumed to comprise ablation of a portion of a myocardium 16 of the heart of a human patient 18. However, it will be understood that embodiments of the present invention are not just applicable to this specific procedure, and may include substantially any ablation procedure on biological tissue.

In order to perform the ablation by RF ablation, physician 14 inserts a probe 20 into a lumen of the patient, so that a distal end 22 of the probe enters the heart of the patient. Distal end 22 comprises one or more electrodes 24 mounted on the outside of the distal end, the electrodes contacting respective locations of the myocardium. Probe 20 has a proximal end 28. Distal end 22 of the probe is described in more detail below with reference to FIG. 2A, FIG. 2B, FIG. 2C and FIG. 2D. Affixed to the patient's skin, for example, on the patient's back, abdomen or thigh, is a large grounding patch (not shown). RF energy delivered by the probe 20 passes from the electrodes 24 through the patient's body to the large grounding patch.

Apparatus 12 is controlled by a system processor 46, which is located in an operating console 48 of the apparatus. Console 48 comprises controls 49 which are used by physician 14 to communicate with the processor. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster, of Diamond Bar, CA, uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62. The progress of the ablation performed with apparatus 12 is typically also displayed on screen 62, as a graphic 64 and/or alphanumeric data 66.

In order to operate apparatus 12, processor 46 communicates with a memory 50, which has a number of modules used by the processor to operate the apparatus. Thus, memory 50 comprises a temperature module 52, a power control module 54, a force module 56, and an irrigation module 58, the functions of which are described below. The modules may comprise hardware as well as software elements.

Figures 2A, 2B, 2C:
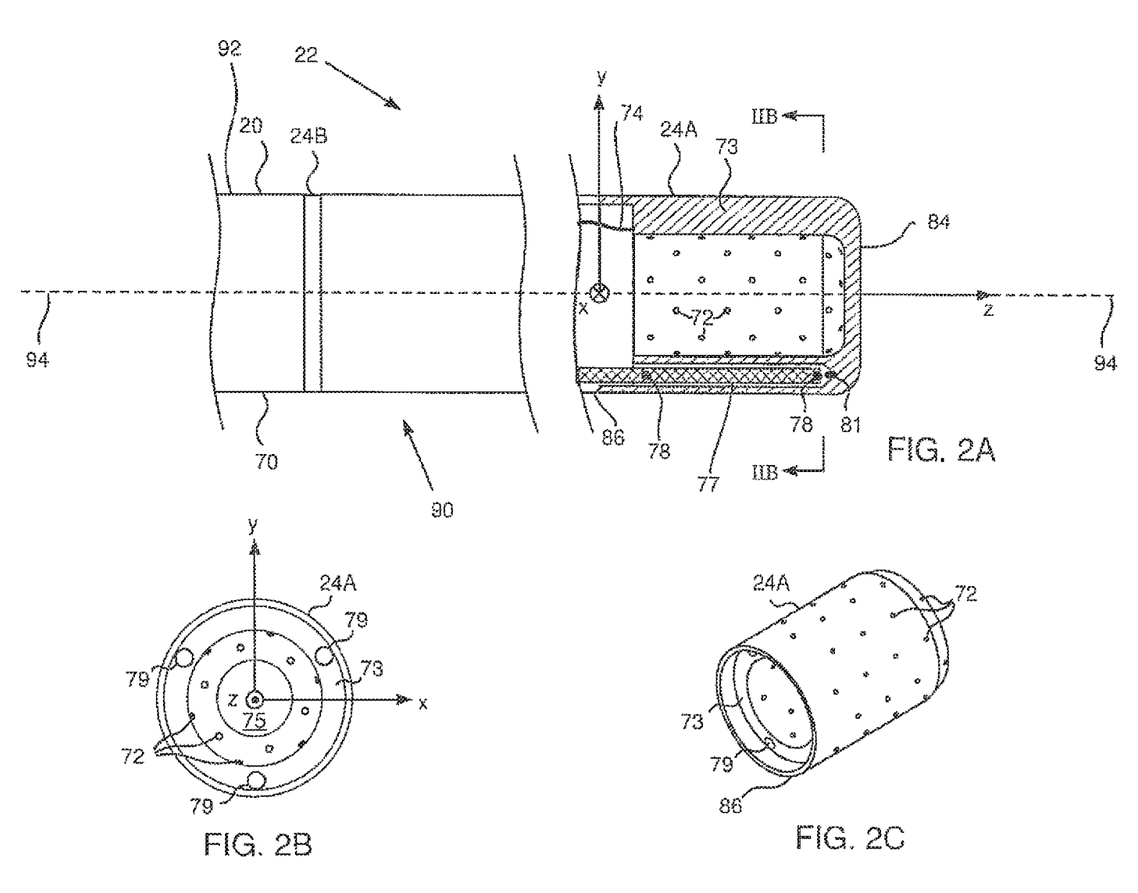
FIGS. 2A, 2B, 2C, and 2D schematically illustrate a distal end of a probe used in the system, according to an embodiment of the present invention.
Figure 2D:
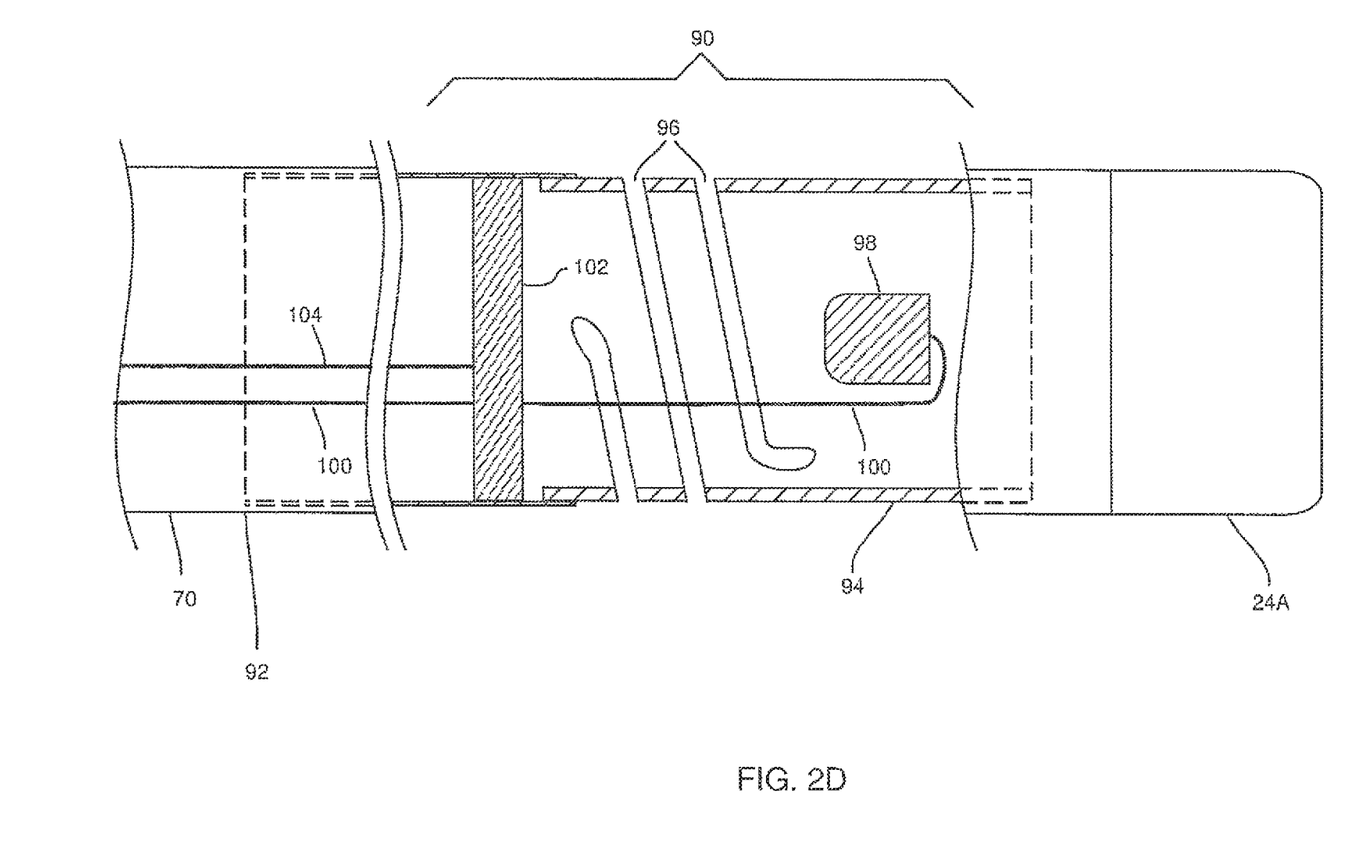

FIG. 2A, FIG. 2B, FIG. 2C, and FIG. 2D schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, FIG. 2C is a perspective view of a section of the distal end and FIG. 2D is a schematic cross-sectional view of a force sensor 90 incorporated into a proximal portion 92 of the distal end. An insertion tube 70 extends along the length of the probe and is connected at the termination of its distal end to a conductive cap electrode 24A, which is used for ablation. Conductive cap electrode 24A is herein also termed the ablation electrode. Cap electrode 24A has an approximately plane conducting surface 84 at its distal end and a substantially circular edge 86 at its proximal end. Proximal to ablation electrode 24A there are typically other electrodes such as an electrode 24B. Typically, insertion tube 70 comprises a flexible, biocompatible polymer, while electrodes 24A, 24B comprise a biocompatible metal, such as gold or platinum, for example. Ablation electrode 24A is typically perforated by an array of irrigation apertures 72. In one embodiment there are 36 apertures 72, distributed evenly over electrode 24A.

An electrical conductor 74 conveys radio-frequency (RF) electrical energy from ablation module 54 (FIG. 1), through insertion tube 70, to electrode 24A, and thus energizes the electrode to ablate myocardial tissue with which the electrode is in contact. As described below, module 54 controls the level of RF power dissipated via electrode 24A. During the ablation procedure, irrigation fluid flowing out through apertures 72 irrigates the tissue under treatment, and the rate of flow of fluid is controlled by irrigation module 58. The irrigation fluid is delivered to electrode 24A by a tube (not shown in the diagram) within insertion tube 70.

Temperature sensors 78 are mounted within conductive cap electrode 24A at locations that are arrayed around the distal tip of the probe, both axially and circumferentially. In a disclosed embodiment considered herein, cap 24A contains six sensors, with one group of three sensors in a distal location, close to the tip, and another group of three sensors in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. Sensors 78 are connected by leads (not shown in the diagram) running through the length of insertion tube 70 to provide temperature signals to temperature module 52.

In a disclosed embodiment cap 24A comprises a side wall 73 that is relatively thick, on the order of 0.5 mm thick, in order to provide the desired thermal insulation between temperature sensors 78 and the irrigation fluid inside a central cavity 75 of the tip. The irrigation fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. Patent Application 2014/0171821, to Govari et al., whose disclosure is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of xyz orthogonal axes, where an axis 94 of the distal end corresponds to the z axis of the set. For simplicity and by way of example, the y axis is assumed to be in the plane of the paper, the xy plane is herein assumed to correspond to the plane defined by circle 86, and the origin of the xyz axes is assumed to be the center of the circle.

FIG. 2D is a schematic, sectional view of force sensor 90, according to an embodiment of the present invention. Sensor 90 comprises a spring 94, herein assumed to comprise a plurality of helices 96, connecting cap 24A to proximal end 92. A position sensor 98 is fixed to the distal side of spring 94, and is herein assumed to comprise one or more coils coupled by conductors 100 to force module 56.

An RF transmitter 102, typically a coil, is fixed to the proximal side of spring 94, and the RF energy for the transmitter is provided from force module 56 via conductors 104. The RF energy from the transmitter traverses sensor 98, generating a corresponding signal in conductors 100 of the sensor.

In operation, as force is exerted on cap 24A sensor 98 moves relative to transmitter 102, and the movement causes a change in the signals of the sensor. Force module 56 uses the change in signal of the sensor to provide a metric of the force on cap 24A. The metric typically provides the force in magnitude and direction.

A more detailed description of a sensor similar to sensor 90 is provided in US Patent Application 2011/0130648, which is incorporated herein by reference.

Returning to FIG. 1, temperature module 52 receives signals from the six sensors 78 within cap 24A, and uses the signals to determine a maximum value of the six measured temperatures. The temperature module is configured to calculate the maximum temperature at a fixed rate, herein assumed to be every 33 ms, but other embodiments may calculate the maximum temperature at higher or lower rates. In some embodiments the maximum temperature is determined at a frequency of at least 30 Hz. The calculated maximum temperature is herein also termed the measured temperature, and the measured temperature registers as the temperature of the tissue being ablated. The temperature module passes the measured temperature value to power control module 54.

Power control module 54 provides RF power to cap 24A in a range of 1 W to 100 W. In embodiments of the present invention the module can be configured to provide a maximum RF power to cap 24A that can be set within a range of 70 W-100 W.

The power control module also measures an impedance of cap 24A. The impedance is measured at a predefined rate, herein assumed to be every 500 ms, but other embodiments may measure the impedance at a lower or higher rate.

The maximum power, and the time period for which the power is delivered, is selected by physician 14. The actual power delivered is determined by the measured temperature received from temperature module 52, as described below.

Typically, during an ablation session, the impedance of cap 24A decreases. Embodiments of the present invention also check if the impedance increases from a previous impedance measurement by more than a pre-set value, herein assumed to be 70, although other embodiments may use larger or smaller values of impedance increase for the pre-set value. An increase of impedance typically occurs if there is an unwanted change in the tissue being ablated, such as charring or steam popping. If the impedance increases by more than the pre-set value, the power control module is configured to stop the RF delivery to cap 24A.

Notwithstanding the powers selected by the physician, the power control module is configured to reduce the power delivered, typically by between approximately 5% and approximately 95%, if the measured temperature received from the temperature module reaches or exceeds a maximum allowable temperature that is set by physician 14.

Typically, exceeding the maximum allowable temperature causes undesirable effects such as charring, coagulation on cap 24A, and/or steam pops in the tissue being ablated.

As explained above, force module 56 is able to measure the force on cap 24A. In an embodiment, the allowable force for an ablation is in the range of 5 g-35 g.

Irrigation module 58 governs the rate at which irrigation fluid is delivered to the catheter tip. In some embodiments of the present invention it may be set within the range of 8-45 ml/min.

Figure 3:
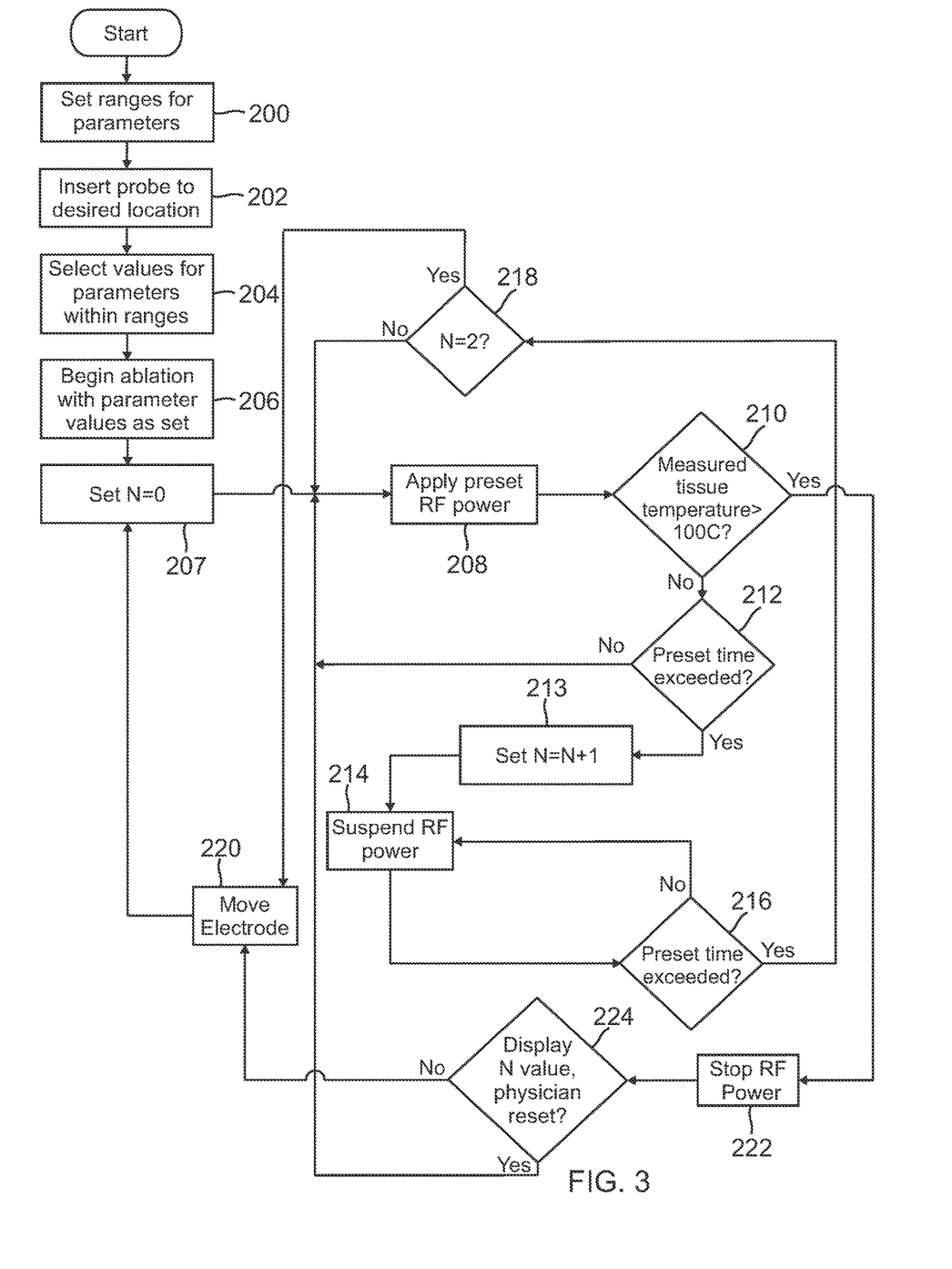
FIG. 3 is a flowchart of steps performed during an ablation session using the system.

FIG. 3 is a flowchart of steps performed in operation of apparatus 12 during an ablation session, according to an embodiment of the present invention. In an embodiment of the present invention, an ablation session comprises at least three stages: a first stage of a first time period during which a first RF target power applies, followed by a second stage of a second time period during which the application of RF power is abated or suspended, and further followed by a third stage of a third time period during which a second RF target power applies. The target powers within each time period are maximum RF powers which may be delivered by power control module 54.

As RF energy of a high power is delivered to the ablation electrode for a predetermined short duration, for example, 4-5 seconds, in the first stage of an ablation session, tissue between the electrode and the grounding patch elsewhere on the patient's body experiences resistive heating at a rate proportional to the square of current density such that current density is the highest in the tissue immediately adjacent the electrode because of its smaller surface area relative to the grounding patch. Thus, the tissue immediately surrounding the electrode is subjected to resistive heating from which a lesion is formed within the predetermined short duration when the tissue is sufficiently heated to cause necrosis.

In a second stage of the ablation session, the application of RF power to the ablation electrode is abated or suspended for a predetermined duration, for example, between about 4 and 10 seconds, such that tissue surrounding the lesion is subjected to conductive heating from the lesion as the resistive heat of the lesion spreads to the surrounding tissue.

In a third stage of the ablation session, while resistive heat continues to be conducted into the surrounding tissue and before such resistive heat dissipates significantly or completely, a second application of RF energy for a predetermined short duration, for example, 4-5 seconds, creating additional resistive heating in the lesion causes further conductive heating in the surrounding tissue which leads to necrosis that advantageously increases the size of the lesion into the surrounding tissue, including increased surface area and increased depth.

Figure 4A:
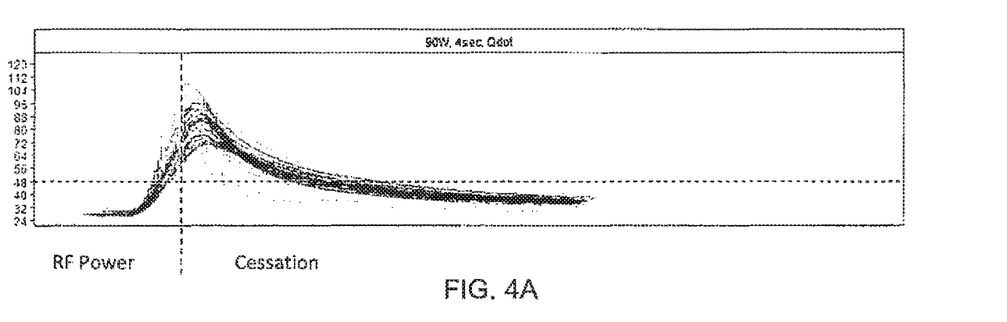
FIG. 4A illustrate measured tissue temperature during an application of RF power of 90 W for a short duration of 4 seconds.

In accordance with embodiments of the present invention, tissue subjected to high RF power for short duration exhibits thermal latency where temperature of ablated tissue continues to increase after abatement of RF ablation at high power. In FIG. 4A, RF power of 90 W is applied to tissue for 4 seconds during which tissue temperature rapidly increases at a generally steady rate (i.e., generally linear slope) to a temperature of 48 C where necrosis begins and initial lesion forms. Notably, after RF power is abated or suspended tissue temperature continues to increase to a range between about 72c-96 C or greater at about the same steady rate for at least another 2 seconds. Tissue temperature is then constant at a peak for about 1-2 seconds before tissue temperature begins to decrease at about 4 seconds after abatement. The tissue temperature decreases at a significantly slower rate compared to the rate of tissue temperature increase during ablation.

The continued increase of tissue temperature after ablation abatement due to resistive heating advantageously facilitates conductive heating of tissue surrounding the lesion which enables, or at least prepares and primes the lesion to increase in surface area and depth upon the further application of high RF power to the lesion, for example, a second application of ablation with 90 W at 4 seconds.

Thermal latency in tissue at 3 mm depth (as measured by a thermocouple sensor) is approximately 10 secs for an application of 90 W for 4 seconds. Approximately 90% of the heat in the tissue is dissipated within 4 seconds at 3 mm depth. The four seconds of RF power suspension between first and second applications of 90 W for 4 secs allows heat dissipation and provides a safer condition for overlapping ablation or ablation of the same lesion.

Figure 4B:
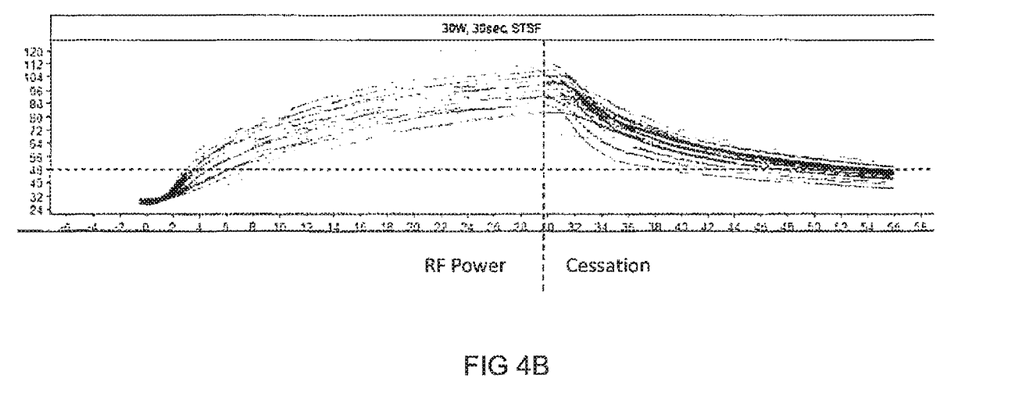
FIG. 4B illustrate measured tissue temperature during an application of RF power of 30 W for a longer duration of 30 seconds.

In contrast, application of low RF power for longer duration results in significantly reduced thermal latency. As shown in FIG. 4B, the application of RF power at 30 W for 30 seconds results in little, if any, continued increase in tissue temperature after abatement or suspension of RF power. Although tissue temperature during ablation may peak at higher temperatures, tissue temperature drops within about 2 seconds after abatement of RF power. Thus, there is less thermal latency available for conductive heating of tissue surrounding the lesion to increase surface area or depth.

Notably, the abatement or suspension of RF power between two short durations or "pulses" of high RF power minimizes the risk of complications from excessive heating of the tissue, for example, steam pops and/or charring. Thus, a balance is achieved between excessive heating causing unintended damage to tissue and sufficient heating to create desirable thermal latency for productive conductive heating in the tissue surrounding the lesion to increase lesion surface area and depth.

Application of high RF power in short durations or "pulses" of approximately 4-5 seconds is desirable because the short duration minimizes variations in the physician's use and operation of the catheter. Shorter durations can minimize inadvertent movement of the catheter tip and/or inadvertent inconsistencies in the application of pressure of the catheter tip against tissue. In ablation sessions creating lesions forming a continuous line of block, such as in pulmonary vein isolation procedures, the physician's consistency in his or her use of the catheter is an important factor in forming successful continuous line of block. Thus, high RF power enables short ablation durations for greater consistency and thus higher success rates in patient treatment.

It is understood that thermal energy is measured in joules (J) within the International System of Units (SI). One joule is the quantity of energy equivalent to a 1 Newton force applied through a distance of 1 meter. Thus, it is the energy needed to accelerate a mass of 1 kg at 1 m/s2 through a 1 m distance in space. 1 J=1 kg×m2/s2. Energy is the result of power multiplied by the pulse duration (J=W*s), so control of energy includes controlling two variables: time and power. Accordingly, some embodiments of the present invention can also be described as the application of pulses of about 360 joules of energy per pulse to tissue via an electrode, where 360 joules translate into a range of power at 75 W in a duration of 5 seconds to power at 95 W in 3.8 seconds, to provide resistive heating with sufficient thermal latency.

Where the ablation electrode is a distal tip electrode, the diameter of the electrode is about 2.5 mm, in forming lesions having a depth of about 3.5 mm that can be increased to a depth of about 4.5 mm with pulses of high RF power in short duration, as described herein.

With reference to FIG. 4A, in a range setting step 200, ranges for each of the variable parameters referred to above are set. In one embodiment the ranges are set as shown in Table I. Table II below lists additional parameters that may be incorporated into the ablation session, including irrigation rate ranging between about 8-45 ml/min, and allowable force at the ablation electrode against tissue ranging between 5 g-50 g.

TABLE I

| Stage | RF Power | Duration | Tissue Reaction |
|---|---|---|---|
| 1 | 75 W-95 W | 4-5 secs | resistive heating of tissue immediately surrounding electrode resulting in necrotic formation of a lesion of an initial depth, e.g., 3.5 mm |
| 2 | 0 | up to 10 secs | Thermal latency in lesion, and conductive heating of tissue surrounding the lesion |
| 3 | 75-95 W | 4-5 secs | further resistive heating of the lesion resulting in necrosis of the surrounding tissue which increases size of the lesion, including an increased subsequent depth, e.g., 4.5 mm |

TABLE II

| Parameter | Range |
|---|---|
| Allowable Force | 5 g-50 g |
| Irrigation rate | 8-45 ml/min |

Range setting step 200 is implemented before physician 14 performs an ablation.

At the beginning of an ablation session, in a probe introduction step 202, physician 14 inserts probe 20 into a desired location in myocardium 16, using the tracking system incorporated into apparatus 12.

In a select value step 204, prior to performing the ablation procedure, physician 14 selects values of the parameters listed in at least Table I, and may include those of Table II, that are to be used in the procedure, and uses controls 49 to provide the values to the system.

In a begin RF delivery step 206, the ablation session begins, by physician 14 initiating operation of apparatus 12. The ablation session uses the parameter values selected in step 204, in order to perform the ablation. Typically, during the ablation session, screen 62 displays values of the parameters listed in at least Table I, if not also Table II, to the physician. Screen 62 may also be configured to display to the physician, by methods which are known in the art, the progress of the RF delivery. The display of the progress may be graphical, such as a simulation of the dimensions of the lesion as it is produced by the ablation, and/or alphanumeric.

During the RF delivery procedure the system uses the power control module to perform a number of checks on the progress of the procedure, as shown in the flowchart by decision steps 210, 212, 216, 218 and 224, as shown in FIG. 3.

With reference to FIG. 3, the power control module in step 207 initiates a counter with N=0. In step 208 the power control module applies the first pulse of high RF Power as a first stage of the ablation session. In decision step 210, the power control module checks if the measured tissue temperature exceeds 100 C as a safety measure. If the measured tissue temperature is not greater than 100 C, the power control module in decision step 212 checks if the preset short duration of the first pulse has been achieved. If it has not, the application of the first pulse continues. If it has, the power control module in step 213 increases the count by one and in step 214 suspends RF power, as a second stage of the ablation session.

In decision step 216, the power control checks if the preset time period of suspension has been achieved. If it has, the power control module in decision step 218 checks if count N=2. If yes, the power control module in step 220 provides a prompt (visual and/or audio) to the physician to move the electrode to another tissue location. If no, the power control module returns to step 208 to apply the second pulse of high RF power as a third stage of the ablation session and proceeds through the decisions steps 210 and 212 as described above until in decision step 218 the count N=2, at which occurrence the power control module in step 220 prompts the physician to move the electrode to another tissue location.

Whenever the measured tissue temperature in decision step 210 exceeds 100 C, the power control module as a safety measure stops RF power in step 222 and in decision step 224 the N count is displayed to the physician and the physician is queried whether or not to reset the system. In some embodiments, step 222 may involve reducing RF power rather than stopping RF power.

Figure 5A:
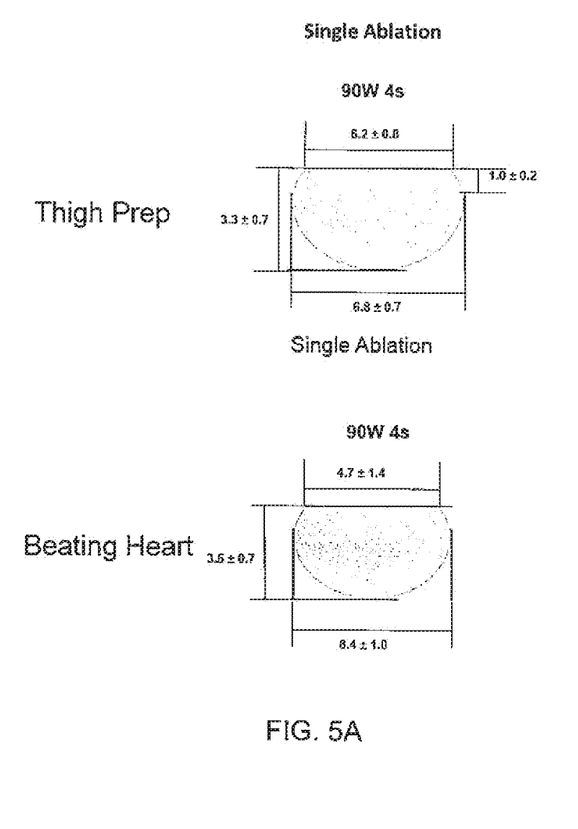
FIG. 5A illustrates lesion surface area and lesion depth resulting from ablation using a single application of high RF power in short duration.
Figure 5B:
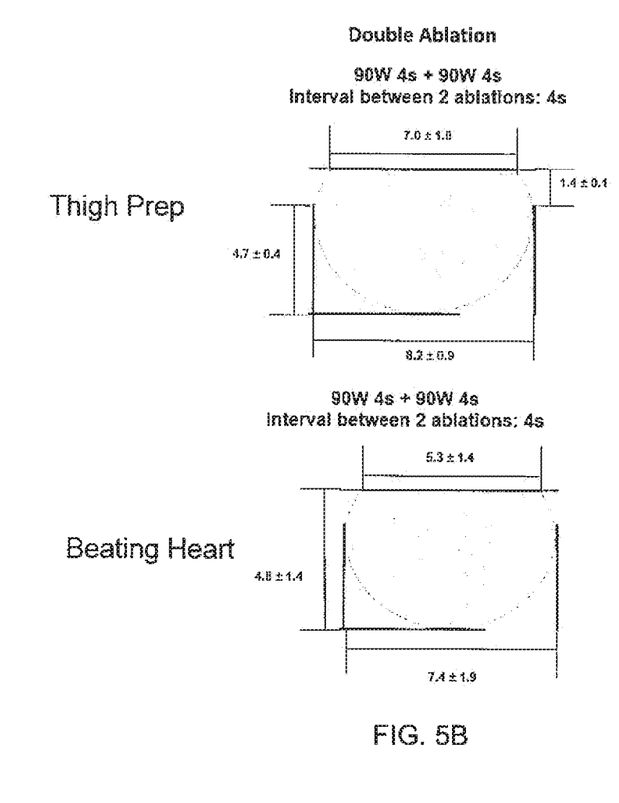
FIG. 5B illustrates greater lesion surface area and greater lesion depth resulting from ablation using two applications of high RF power in short duration separated by an interval of RF power suspension.

As shown in FIG. 5A and FIG. 5B, lesions formed in thigh tissue and beating heart tissue in a single application of 90 W for 4 secs has a lesser width and a lesser depth in contrast to lesions formed in thigh tissue and beating heart tissue in "double" applications of 90 W for 4 secs separated by an interval of ablation suspension for 4 secs.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method of ablation comprising:
    inserting a catheter into a subject, the catheter having an ablation electrode configured for tissue contact;
    performing an ablation session on the tissue for a predetermined total duration of time less than about 18 seconds, including:
        applying resistive heating to the tissue by radiofrequency (RF) power via the electrode within a range of about 75 W-95 W for a first duration of about 4 seconds to form a lesion with a depth of about 3.5 mm;
        suspending application of RF power to the electrode for a second duration no greater than 10 seconds, during which a temperature of the lesion continues to increase, to allow tissue surrounding the lesion to heat by conduction from the lesion;
        measuring temperature of the tissue at least every 33 ms at a depth of about 3 mm to determine dissipation of about 90% of heat of the tissue within about 4 seconds; and
        while the tissue surrounding the lesion remains heated by conduction from the lesion, reapplying resistive heating by RF power via the electrode within the range of about 75 W-95 W for a third duration of about 4 seconds to the lesion to increase depth of the lesion to about 4.5 mm into the surrounding tissue.

2. The method of claim 1, wherein the total duration is less than about 13 seconds.

3. The method of claim 1, wherein the RF power in the first duration and in the third duration is about 90 W.

4. The method of claim 1, wherein a rate of temperature increase of the tissue in the first duration is greater than the rate of temperature decrease of the tissue in the second duration.

5. The method of claim 1, wherein the rate of temperature increase of the tissue in the first duration is generally linear.

6. The method of claim 1, further including measuring impedance of the tissue every 500 ms.

* * * * *